United States Patent [19]

Blurton et al.

[11] 4,052,268

[45] Oct. 4, 1977

[54] METHOD FOR THE DETECTION AND MEASUREMENT OF NITRIC OXIDE, NITROGEN DIOXIDE AND MIXTURES THEREOF

[75] Inventors: Keith F. Blurton, Yorktown, N.Y.; John M. Sedlak, Norwalk, Conn.

[73] Assignee: Energetics Science, Inc., Elmsford, N.Y.

[21] Appl. No.: 675,062

[22] Filed: Apr. 8, 1976

Related U.S. Application Data

[62] Division of Ser. No. 517,648, Oct. 24, 1974, abandoned.

[51] Int. Cl.² ............................................. G01N 27/46
[52] U.S. Cl. .................................. 204/1 T; 204/195 R
[58] Field of Search ..................... 204/1 N, 1 R, 195 R

[56] References Cited

U.S. PATENT DOCUMENTS

| | | | |
|---|---|---|---|
| 3,622,487 | 11/1971 | Chand et al. | 204/1 N |
| 3,763,025 | 10/1973 | Chand | 204/1 N |
| 3,776,832 | 12/1973 | Oswin et al. | 204/195 R |
| 3,821,090 | 6/1974 | Topol et al. | 204/1 N |
| 3,824,167 | 7/1974 | Oswin et al. | 204/195 R |

Primary Examiner—T. Tung
Attorney, Agent, or Firm—Larson, Taylor and Hinds

[57] ABSTRACT

In the detection and measuring of NO, $NO_2$ and mixtures thereof, a unit comprising in combination intake means, an electrochemical cell, means for drawing the gas through said intake means and into said electrochemical cell at a controlled flow rate, readout means for reading the quantity of gas detected, the electrochemical cell comprising an anode, a cathode, a reference electrode at which substantially no current flows and an aqueous electrolyte in contact with said anode, cathode and reference electrode, means for exposing said anode to said gas, means for maintaining said anode at a fixed potential relative to the reference electrode in excess of 1.5 V up to about 1.9 V with respect to a reversible hydrogen electrode in said electrolyte of said first electrochemical cell, the anode of said first electrochemical cell comprising a gold catalyst bonded to a hydrophobic material to provide a diffusion electrode.

6 Claims, 5 Drawing Figures

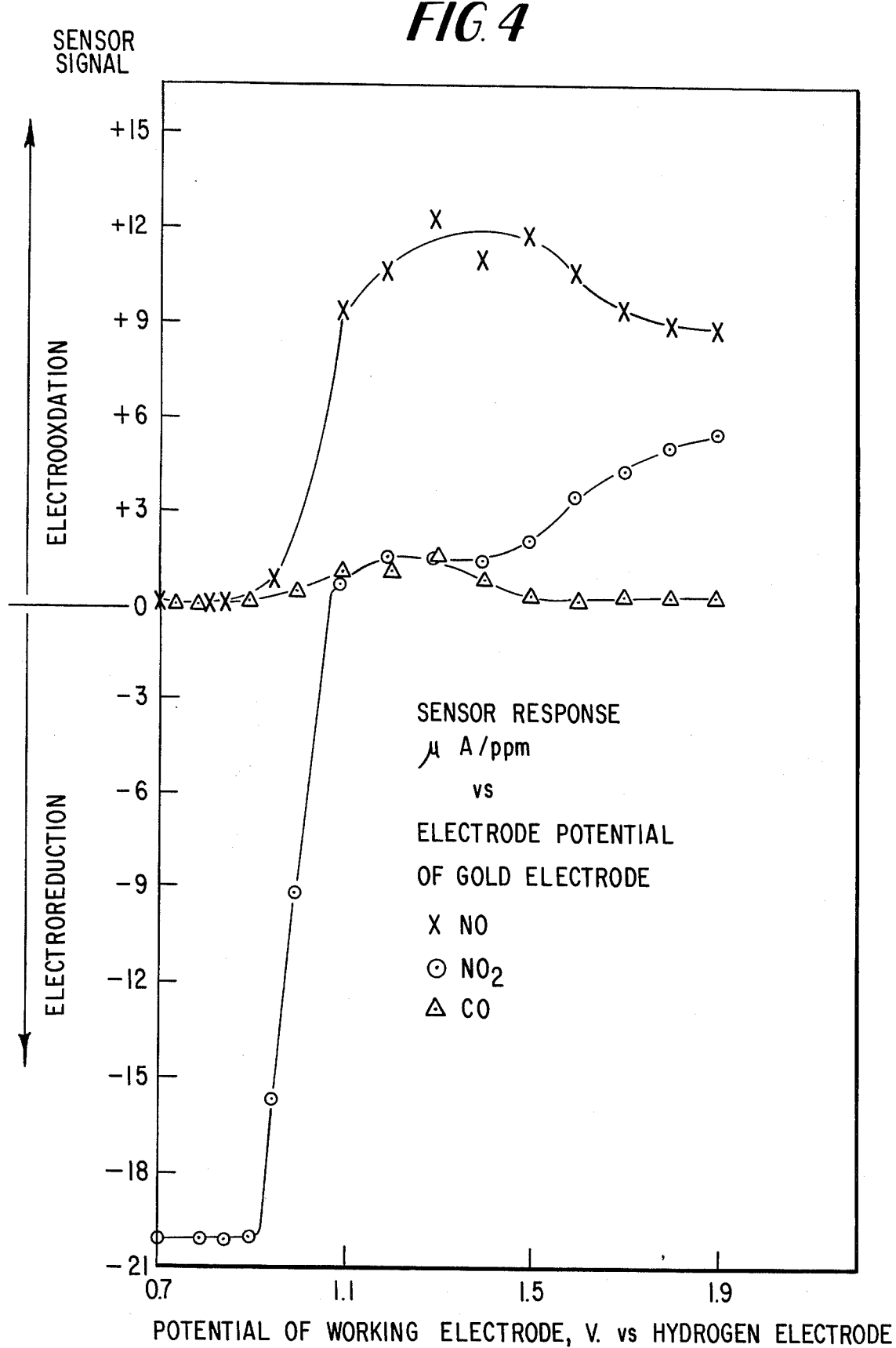

4,052,268

METHOD FOR THE DETECTION AND MEASUREMENT OF NITRIC OXIDE, NITROGEN DIOXIDE AND MIXTURES THEREOF

This is a division of application Ser. No. 517,648, filed Oct. 24, 1974, now abandoned.

BACKGROUND OF THE INVENTION

1. Field of the Invention

The present invention relates to a device and method for the detection and measurement of nitric oxide, nitrogen dioxide or nitrogen oxides (NOx) in a gaseous medium. More particularly, the invention is directed to the detection of these oxides of nitrogen in the presence of high concentrations of carbon monoxide.

2. Discussion of the Prior Art

In recent times, a greater awareness has developed regarding the dangers of air pollution, particularly in urban or industrialized areas. Amongst the principal contributions to air pollution are the products of incomplete combustion such as carbon monoxide, hydrocarbons, carbonaceous particulate matter, etc. Attempts to eliminate these pollutants through more efficient combustion processes has resulted in a frustrating dilemma for the severe oxidation conditions ordinarily employed in more efficient combustion processes increases noxious NO and $NO_2$ gases produced over and above that ordinarily formed as combustion by-products. It is not surprising, therefore, that most major cities yearly average nitrogen dioxide levels are approaching levels known to be harmful to health.

In order to meet the needs arising in connection with pollution control of NO and $NO_2$, extensive activity has been directed to the development and production of equipment useful in solving this problem. A problem encountered in the development of such equipment is the difficulties experienced in the detection of low concentrations of NO and $NO_2$ in the presence of high concentration of CO, a frequently encountered situation. For instance, Oswin et al in U.S. Pat. No. 3,776,832 teaches use of a three electrode system employing a gold working electrode and a fixed potential of 1.0 V to 1.3 V for the detection of nitric oxide. While an effective sensor of nitric oxide in other gaseous media, it has its shortcomings in the detection of small amounts of nitric oxide in gaseous mixtures containing high concentrations of carbon monoxide.

Also, another problem which must be confronted in the search for solutions to this problem is the acknowledged difficulty of measuring NO in the presence of $NO_2$. Although systems may exist which may be considered functionally successful, actual utilization in practical applications has quite often been thwarted due to the cost and complexity of such equipment.

The general criteria applied to measuring and testing equipment such as that of the present invention includes requisites for portability, non-prohibitive cost and accuracy in measuring the quantity of the gas detected. In the prior art, it has been found difficult to simultaneously fulfill all of these requirements. Increasing the accuracy of measuring equipment has inherently involved an increase in either the size or the complexity of such equipment thereby disadvantageously affecting either the cost or portability or both. Quite often, problems related to the simultaneous provision of these features have been decisive in obstructing the practical development and utilization of particular detection apparatus.

OBJECTS AND GENERAL DESCRIPTION OF THE INVENTION

Accordingly, a primary object of the present invention is to provide a compact, inexpensive, and easy-to-operate device for accurately and reproducibly detecting and quantitatively determining the level of NO and $NO_2$ and mixtures thereof in a specific environment.

Another object of this invention is to provide a compact, inexpensive, and easy-to-operate device for accurately and reproducibly detecting and quantitatively determining the low concentrations of NO, $NO_2$ and mixtures thereof in the presence of high concentrations of CO.

It is another object of this invention to provide a device for accurately measuring low concentrations of NO in the presence of $NO_2$.

Another object of this invention is to provide methods for electrochemically detecting low concentrations of NO, $NO_2$ and mixtures thereof in a gaseous medium.

The aforesaid objects of the present invention are obtained by an apparatus for detecting and measuring a gas selected from NO, $NO_2$ and mixtures thereof in the presence of substantial concentrations of CO comprising in combination, intake means, an electrochemical cell, means for drawing said gas through said intake means and into and through said electrochemical cell at a controlled flow rate, and read-out means for reading the quantity of detected gas. The electrochemical cell comprises a gold anode that provides a catalytic site for electrooxidation of the gas being detected; a cathode, a reference electrode at which substantially no current flows, and an electrolyte in contact with the anode, cathode and reference electrode and means for exposing said anode to the gas to be detected. The anode of the cell is maintained by suitable means such as a potentiostat at a fixed potential-relative to the potential of the reference electrode of in excess of 1.5 up to about 1.9 V, preferably about 1.6 to 1.9 V, with respect to a reversible hydrogen electrode in said electrolyte. It has been found that the sensor of the invention with its gold working electrode at this fixed potential is able to detect very small amounts of NO or $NO_2$ in the presence of high concentrations of CO and other gases. In this potential range of in excess of 1.5 to 1.9 V the signals due to NO and $NO_2$ in the sensor of the invention are significantly large while the signal due to CO is negligible if at all. In addition to CO the following gases also give a negligible signal with the gold catalyzed electrode in this potential range: methane, ethane, propane, hydrogen, $N_2O$, etc. These gases like CO, therefore, will not influence the current produced by NO and $NO_2$ contained in admixture therewith.

The means for drawing gas through the intake means into the cell will effectively pass a predetermined quantity of gas per unit time to a predetermined working electrode surface area, thus assuring continuous accuracy in the quantitative measurement. Preferably, the quantity of gas fed to the anode surface is controlled by a constant flow control means of the conventional type which feeds the gas sample to the electrochemical cell at a constant rate. Pumping or suction means are normally employed to draw the gas sample through the intake means, the electrochemical cell, and flow control means in metered amounts. Preferably the anode chamber will define a labyrinthine path as is described in the electrochemical cell of U.S. Pat. No. 3,776,832, hereby incorporated by reference, through which the gas sample is passed to the working electrode surface. Other designs can be employed, it only being essential that the geometric working electrode surface area remains constant, or substantially constant, and is fed with a predetermined quantity of gas over a predetermined period of time. In this regard it is to be noted that insofar as the actual gas being detected is concerned, it is immaterial whether the flow rate is high or low.

The anode of the electrochemical cell is comprised of catalyst capable of catalyzing electrooxidation of NO and $NO_2$, bonded to a suitable hydrophobic material, such as unsintered polytetrafluoroethylene (PTFE) to provide a light weight diffusion electrode. The hydrophobic material may take the form of a binder for the catalyst, a sheet support therefor or both. For instance, catalytic gold may be deposited as a layer directly to the surface of a hydrophobic sheet support or the gold may be admixed with a suitable hydrophobic binder and the admixture applied as a layer to a suitable support as, for instance, a suitable hydrophobic material such as PTFE, carbon or a metal. When an admixture of catalyst and hydrophobic binder is employed it can be supported with any suitable porous support substrate say of plastic, carbon, metal and the like. Suitable hydrophobic binder and/or support substrate materials include hydrophobic fluorocarbons such as polytetrafluoroethylene, polychlorotrifluoroethylene or the like, as well as less hydrophobic materials including polyacrylonitrile, polyvinylchloride, polyvinylalcohol, carboxymethyl cellulose, or the like. As will be further apparent to one skilled in the art, when the support substrate is a hydrophobic material such as PTFE, the hydrophobic material must be oriented in the cell in order that the catalyst is in contact with the gas sample, with the catalytic layer being in contact with the electrolyte.

The specific structure of the cathode employed in the elctrochemical cell is not critical. It is only essential for the sensor that the cathode consist of a material at which electrochemical reduction occurs. The preferred cathode for the sensor is one which provides a site at which oxygen will be electrochemically reduced as, for example, platinum.

The reference electrode of the electrochemical cell must be capable of maintaining a relatively constant potential in the environment of the electrochemical cell. Preferred reference electrodes are Pt-catalyzed air electrodes. The third or reference electrode can be positioned between the anode and cathode, or it can be positioned on the same plane or substrate as the cathode or anode. Preferably, however, in order to obtain greater compactness of the cell and due to optimum ion-transfer characteristics, and the like, the cathode and the third or reference electrode will be part of a common substrate. It is only necessary that the anode, cathode, and third electrode be electrically insulated from each other. Thus, a polymer substrate such as polytetrafluoroethylene can have two separate and distinct portions coated with a catalytic material such as platinum, or an admixture of platinum and PTFE particles. The entire substrate will, therefore, function as both the cathode and reference electrode. As will be more fully apparent hereinafter, various designs or layouts can be used.

Reference electrode, as the term is used herein, defines an electrode at which no, or substantially no, current flows. Accordingly, the reference electrode and working electrode, i.e. the anode must be connected through electronic circuitry, or the like, to preclude or minimize current flow between the reference electrode and working electrode, so as to define and maintain a known reference potential. Although it is virtually impossible to completely eliminate current flow, the reference potential cannot show extensive drift, i.e., more than about ± 25 mV; or rapid drift, i.e., more than ± 5 mV, over a period of 10 seconds. If extensive or rapid drift occurs, a false reading as to the quantity of the detected gas may be obtained. As is apparent, the actual extent of current drift depends upon the accuracy of the measurement needed. If high accuracy is unnecessary, a greater current drift can be tolerated.

When it is desired to detect NO alone, that is, to the exclusion of $NO_2$ and the gaseous medium contains both NO and $NO_2$, as for instance air, a filter or scrubber means should be employed between the sample intake and the electrochemical cell to remove $NO_2$. $NO_2$ tends to electrooxidize and give a signal at 1.6 V, which is the optimum potential at which the anode is fixed for the detection of NO. Illustrative of suitable filters or scrubbers are adsorbents such as fire brick impregnated with triethanolamine, Mallcosorb and the like.

Advantageously, similar other scrubbers or filters are provided between the sample intake and both electrochemical cells for the removal of other interfering gases such as $H_2S$ that may be present in the gaseous medium and which give signals at the fixed potentials. $H_2S$ gives approximately the same signal as NO at 1.6 V and should be removed from gas samples containing same before measurement. Suitable $H_2S$ filters include, for instance, lead acetate and mercuric chloride filters.

The housing of the electrochemical cell can be made of any suitable material which does not form soluble oxidizable products, preferably plastics such as the olefinic polymers. The housing is to be designed to permit the working electrode to have an area exposed to ambient air. The electrolyte which can be either an aqueous acid of aqueous alkaline solution can be free-flowing or trapped in a suitable matrix. In the event a matrix is employed, the matrix material must be sufficiently hydrophilic to permit continuous wetting of the anode and cathode surfaces as well as the surface of the third or reference electrode. Materials such as asbestos, Kraft paper, polyvinylalcohol, polyvinylchloride which has been treated to render it hydrophilic, or the like, can be selected.

In addition to the electrochemical cell, it is necessary that the detecting device include sample intake means and means to control the flow of the gas sample through the cell. The control of the flow rate of the sample can be accomplished in various ways. Thus, the gas sample is received through the intake means of the detecting device and pulled into the electrochemical cell, preferably by means of a suitable pump. The flow rate can be controlled in various ways including a restricted intake orifice positioned between the pump means and the intake means. The flow meter and pump can be of various commercial design and form no part of the present invention. The only criterion is that the pump means have sufficient capacity to pull the gas sample through the electrochemical cell and flow meter. The flow meter must have precision sufficient to measure the volume being carried through the electrochemical cell with reasonable accuracy.

BRIEF DESCRIPTION OF THE DRAWINGS

The detecting device of the present invention will be more readily apparent from the accompanying drawing wherein like numerals are employed to designate like parts. In the drawing:

FIG. 4 is a graph described above showing the significance of the fixed potential of the invention;

DETAILED DESCRIPTION OF PREFERRED EMBODIMENT

Figure 1:
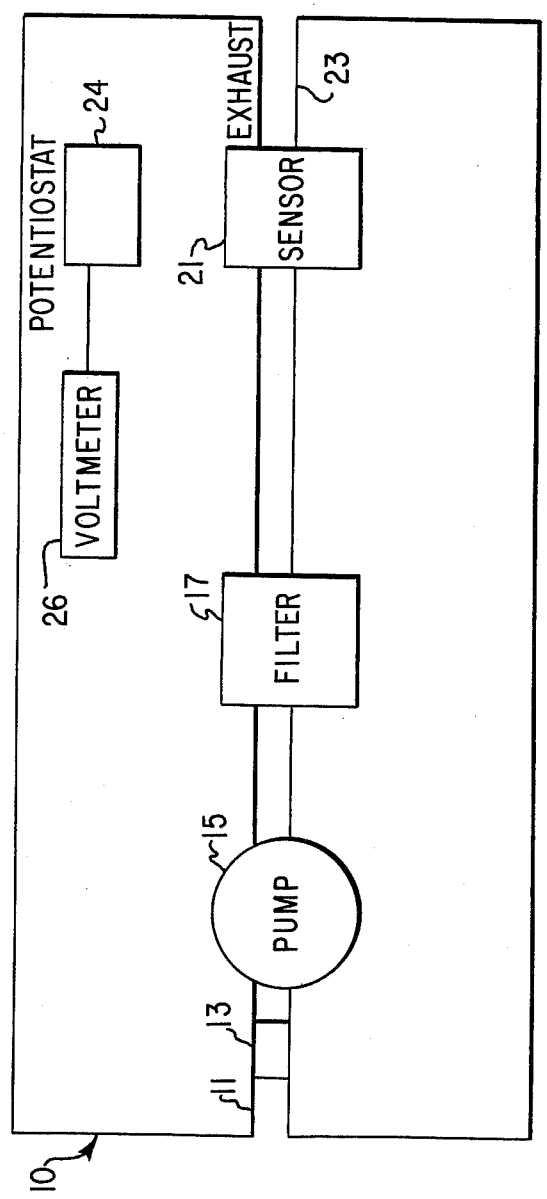
FIG. 1 is a diagrammatic view in block form of a preferred device suitable for use in the detection and measuring of NO and $NO_2$ in the atmosphere.

More specifically, referring to FIG. 1, the detecting device for the measurement of NO and $NO_2$ is positioned within a housing 10. The device includes a sample intake means 11 in direct communication with a flow meter 13 which in turn is in communication with a pump 15. The pump 15 communicates with a Filter 17 containing, for instance, mercuric chloride for the adsorption of $H_2S$. Filter 17 is in direct communication with Sensor 21. Gas flowing through the Sensor 21 exits device via exhaust 23. The Sensor is provided with a potentiostat 24 for maintenance of the fixed relative potential between the anode and the reference electrode of Sensor 21 and a voltmeter 26. The potentiostat is hooked up to an electronic circuit described below which includes an amplifier and voltmeter.

Figure 2:
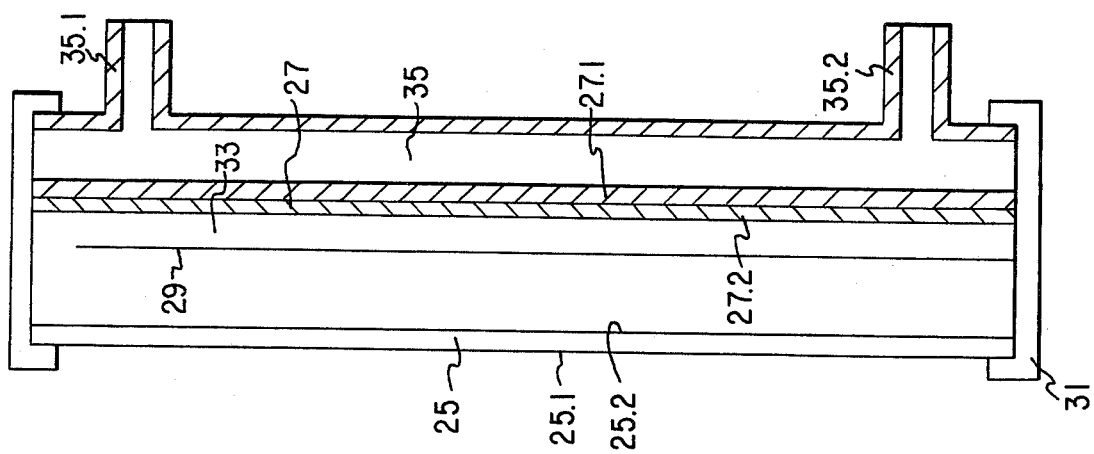
FIG. 2 is a cross-sectional view of an electrochemical cell useful in the detector unit.

Electrochemical cell 21 as seen most clearly from FIG. 2, will include a cathode 25, an anode 27, and a third or reference electrode 29, all positioned within a housing 31. In the embodiment of FIG. 2, the cathode, anode, and third electrode are in contact with a freeflowing electrolyte 33. Adjacent anode 27 is reactant chamber 35 having reactant gas inlet 35.1 which is in direct communication with intake 11 and outlet 35.2. In the embodiment shown, cathode 25 is in direct communication with atmospheric air. Both the anode and cathode are lightweight electrodes comprising a hydrophobic plastic substrate 27.1 and 25.1 in direct contact with reactant chamber 35 in the case of the anode, and with the ambient environment in the case of the cathode, and catalytic layers 27.2 which comprise a mixture of gold powder and polytetrafluoroethylene particles and 25.2 which comprise a mixture of platinum and polytetrafluoroethylene particles. The catalyst layers are in contact with the electrolyte of the cell. The gold is present in a loading of preferably 5-50 $mg/cm^2$, more preferably 5-30 $mg/cm^2$. The ratio of gold to PTFE is preferably 10 to 3 on a weight basis. Reference electrode 29 is a porous, platinum catalyzed PTFE diffusion electrode which is approximately 7 mils thick. A fixed potential of 1.6 volts with respect to a reversible hydrogen electrode in the same electrolyte is maintained on the anode by means of the reference electrode through the potentiostat 24. The anode, cathode and reference electrode of the cell are connected through the electrical circuit, shown in FIG. 3. The electrochemical cell of the Sensor is connected to the circuitry so that the polarity of the working electrode (anode) to the counter electrode (cathode) is positive.

Figure 3:
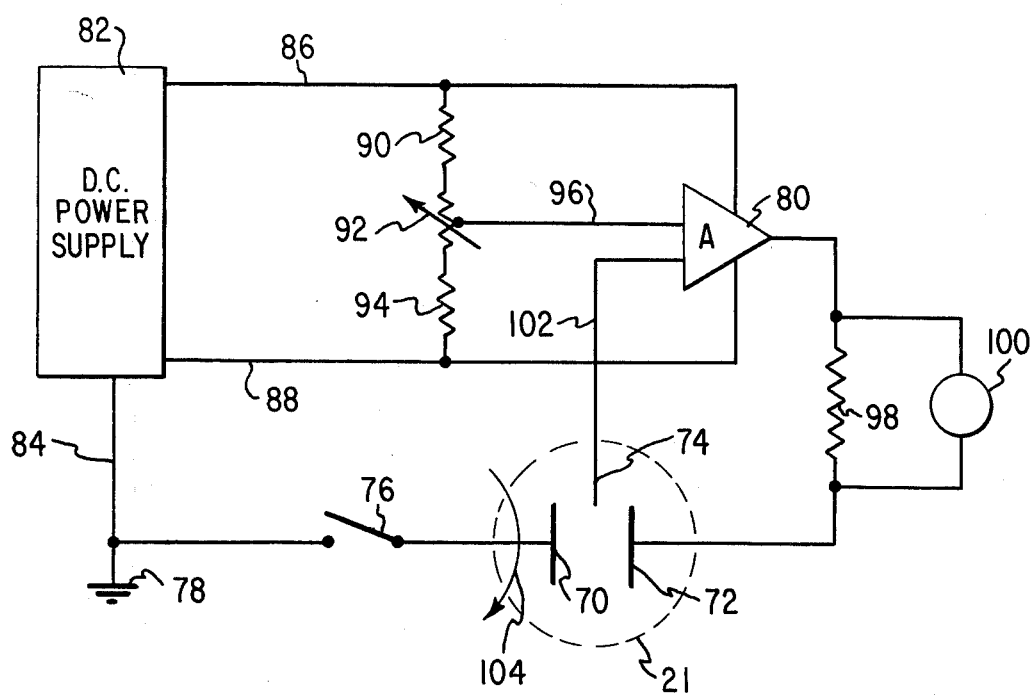
FIG. 3 is a schematic diagram of a potentiostat circuit for controlling operation of the cell and particularly as applied in maintaining a fixed potential between the working electrode and a reference electrode.
Figure 5:
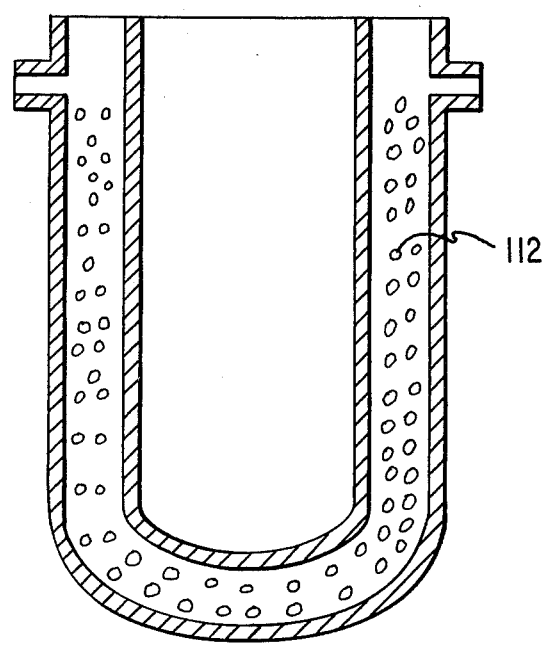
FIG. 5 is a filter unit for incorporation in the device of FIG. 2.

The circuitry whereby the maintenance of a fixed relative potential between the working electrode and reference electrode is shown in FIG. 3. FIG. 3 depicts a potentiostat circuit which is generally arranged in accordance with conventional principles within the knowledge of those skilled in the art and which enables the maintenance of the fixed relative potential between the working electrode and the reference electrode without development of current flow therebetween. The circuit also operates to enable appropriate current flow in the external circuit between the working electrode and the counter electrode when the gas to be detected is reacted within the electrochemical cell.

In FIG. 3, the electrochemical cell 21 is shown schematically as comprising an anode 70, a cathode 72, and a reference electrode 74, with the anode connected through a switch 76 to ground potential 78. The circuit basically comprises an operational amplifier 80 having both the reference electrode 74 and the cathode 72 connected thereto. A DC power supply 82 having a connection 84 to ground potential 78 is connected to the amplifier 80 through leads 86 and 88 with resistors 90, 92, and 94 connected thereacross in parallel between the power supply 82 and the amplifier 80. Resistor 92 comprises a rheostat and is connected to the amplifier 80 through a lead 96 whereby adjustment of the resistor 92 enables adjustment of the fixed relative potential which is to be maintained between the reference electrode 74 and the anode 70. The cathode 72 is connected to the amplifier 80 through a resistor 98 having a voltmeter 100 connected thereacross. The reference electrode 74 is connected to the operational amplifier 80 through a lead 102 and as the relative potential between the reference electrode 74 and the anode 70 develops a tendency to vary from the fixed level established by adjustment of the rheostat 92, the amplifier 80 operates through a negative feedback to maintain constant the relative potential between the anode 70 and the reference electrode 74. The factor creating the tendency to alter the anode-reference electrode fixed relative potential is developed as a result of reaction at the anode 70 of the impurity to be detected, i.e. oxidation of NO and/or $NO_2$ contained within the gas sample flowing across the face of the anode 70 as indicated by the arrow 104. The output current of the operational amplifier 80 will pass through the resistor 98 and will be a result of and related to the level of oxidation occurring at the anode 70. Therefore, the reading taken at the voltmeter 100 will be representative of the oxidation reaction occurring at the anode 70 and the quantity of material oxidized. The voltmeter 100 may be readily calibrated in the known manner to provide determination of the quantity of NO and/or $NO_2$ occurring in the air sample taken, and if the conditions in the anode chamber are in accordance with the teachings previously set forth, appropriate readings may be generated pursuant to the principle of operation provided.

The significance of the fixed potential which is maintained between the working electrode and the reference electrode is better described by reference to the chart of FIG. 4 wherein the signal due to NO, $NO_2$ and CO is shown as a function of the potential. The graph shows that in the potential range of greater than 1.5 V up to 1.9 V the signals (the current) due to NO and $NO_2$ are relatively high while the signal due to CO is very small.

In operation, therefore, assuming the desirability of measuring the concentration of NO in the atmosphere, the atmospheric air containing the noxious impurity is introduced at a metered rate into the NO sensors. The sample is passed through filters 17 and 19 for removal of $H_2S$ and $NO_2$. In the NO Sensor the air sample passes over the anode therein setting off electrooxidation of the NO impurity contained therein. This electrochemical reaction produces a current in the external circuit of the cell thereby enabling detection and measurement of the impurity concentration as by use of a voltmeter.

Two approaches may be taken for the measurement of the concentration of $NO_2$ in the atmosphere. In the first method the air is passed through a filter for the removal of NO and then the resulting filtered air is passed over the anode where it is electrochemically oxidized. This reaction produces a current in the external circuit thereby enabling the $NO_2$ concentration to be measured.

Alternatively $NO_2$ may be measured by subtracting the current due to NO oxidation from that due to NO and $NO_2$. For continuous measurements two sensors are required with the air being passed through an $NO_2$-removal filter prior to entering one of the cells. For non-continuous measurements one sensor can be used and the air stream is alternately passed through a $NO_2$-removal filter and directly into the cell.

It is claimed:

1. A method for electrochemically detecting a gas selected from the group consisting of NO, $NO_2$ and mixtures thereof including the steps of (1) feeding a gaseous sample containing said gas to the anode of an electrochemical cell comprising an anode, a reference electrode, a cathode, and an aqueous electrolyte in contact with said anode, cathode, and reference electrode, said anode comprising a gold catalyst bonded to a hydrophobic material to provide diffusion electrode; (2) maintaining said anode at a fixed potential of in excess of 1.5 up to about 1.9 volts with respect to the potential of the reversible hydrogen couple in the electrolyte of said cell; and (3) measuring the current flowing between said anode and cathode of said cell to quantitatively determine the amount of said NO, $NO_2$ and mixtures therof in said gaseous sample.

2. The method of claim 1 wherein the gas sample is contacted with means for the removal of $H_2S$ prior to feeding of the gas sample to said anode.

3. A method for electrochemically detecting NO including the steps of (1) feeding a gaseous sample containing said gas to the anode of an electrochemical cell comprising an anode, a reference electrode, a cathode and an aqueous electrolyte in contact with said anode, cathode and reference electrode, said anode comprising a gold catalyst bonded to a hydrophobic material to provide a diffusion electrode; (2) maintaining said anode at a fixed potential in excess of 1.5 up to 1.9 volts with respect to the potential of the reversible hydrogen couple in the electrolyte of said cell; and (3) measuring the current flowing between said anode and cathode of said cell to quantitatively determine the amount of NO in said gaseous sample.

4. A method for electrochemically detecting NO in a gaseous sample containing both NO and $NO_2$ including the steps of (1) contacting said gaseous sample containing said gases with filter means for the removel of $NO_2$; (2) feeding the resulting gaseous sample to the anode of an electrochemical cell comprising an anode, a reference electrode, a cathode and an aqueous electrolyte in contact with said anode, cathode and reference electrode, said anode comprising a gold catalyst bonded to a hydrophobic material to provide a diffusion electrode; (3) maintaining said anode at a fixed potential in excess of 1.5 up to 1.9 volts with respect to the potential of the reversible hydrogen couple in the electrolyte of said cell; and (4) measuring the current flowing between said anode and cathode of said cell to quantitatively determine the amount of NO in said gaseous sample.

5. A method according to claim 4 wherein the filter means is firebrick impregnated with triethanolamine.

6. A method for electrochemically detecting $NO_2$ in a gaseous sample containing both NO and $NO_2$ including the steps of (1) contacting said gaseous sample containing said gases with filter means for the removal of NO; (2) feeding the resulting gaseous sample to the anode of an electrochemical cell comprising an anode, a reference electrode, a cathode and an aqueous electrolyte in contact with said anode, cathode and reference electrode, said anode comprising a gold catalyst bonded to a hydrophobic material to provide a diffusion electrode; (3) maintaining said anode at a fixed potential in excess of 1.5 up to 1.9 volts with respect to the potential of the reversible hydrogen couple in the electrolyte of said cell; and (4) measuring the current flowing between said anode and cathode of said cell to quantitatively determine the amount of $NO_2$ in said gaseous sample.

* * * * *